United States Patent [19]
Hassard

[11] Patent Number: 6,117,096
[45] Date of Patent: Sep. 12, 2000

[54] LOWER SPINE PROTECTOR

[76] Inventor: Peter K. Hassard, 5240 Broughton Crescent, Burlington, Ontario, Canada, L7L-3B9

[21] Appl. No.: 09/377,193

[22] Filed: Aug. 19, 1999

[51] Int. Cl.$^7$ ..................................................... A61F 5/00
[52] U.S. Cl. .............................................. 602/19; 128/846
[58] Field of Search .................................... 128/845, 846; 602/5, 19

[56] References Cited

U.S. PATENT DOCUMENTS

| | | | |
|---|---|---|---|
| 4,175,553 | 11/1979 | Rosenberg | 602/19 |
| 4,475,543 | 10/1984 | Brooks | 602/19 |
| 5,179,942 | 1/1993 | Drulias | 602/19 |
| 5,188,586 | 2/1993 | Castel | 602/19 |
| 5,632,723 | 5/1997 | Grim | 602/19 |

*Primary Examiner*—Michael A. Brown

[57] ABSTRACT

A lower spine protector for protecting the lower spine from injury from blows to the lower back region of a user. The lower spine protector includes a pad with a pocket on a back face of the pad. An insert is inserted into the pocket. Elongate flexible waist strap are outwardly extended from the sides of the pad.

17 Claims, 2 Drawing Sheets

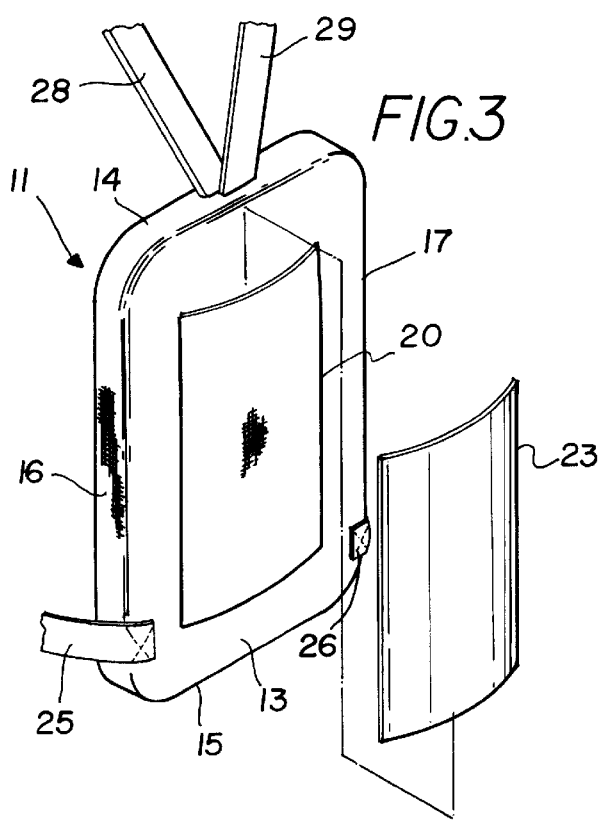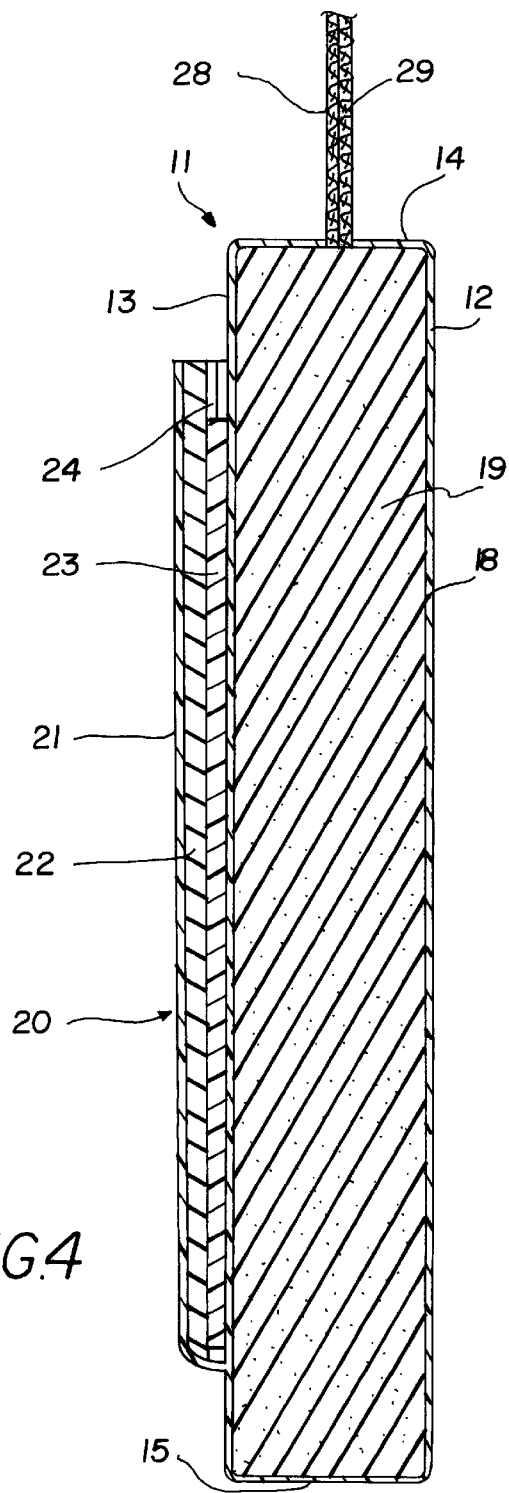

LOWER SPINE PROTECTOR

BACKGROUND OF THE INVENTION

1. Field of the Invention

The present invention relates to lower spine protectors and more particularly pertains to a new lower spine protector for protecting the lower spine from injury from blows to the lower back region of a user.

2. Description of the Prior Art

The use of lower spine protectors is known in the prior art. More specifically, lower spine protectors heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,722,940 by Gaylord, Jr. et al.; U.S. Pat. No. 2,906,260 by Myers; U.S. Pat. No. 5,328,447 by Kapounek et al.; U.S. Pat. No. 4,680,812 by Weigl; U.S. Pat. No. 664,250 by Fitzpatrick; and U.S. Pat. No. Des. 347,692 by McCartney.

While these devices fulfill their respective, particular objectives and requirements, the aforementioned patents do not disclose a new lower spine protector. The inventive device includes a pad with a pocket on a back face of the pad. An insert is inserted into the pocket. Elongate flexible waist strap are outwardly extended from the sides of the pad.

In these respects, the lower spine protector according to the present invention substantially departs from the conventional concepts and designs of the prior art, and in so doing provides an apparatus primarily developed for the purpose of protecting the lower spine from injury from blows to the lower back region of a user.

SUMMARY OF THE INVENTION

In view of the foregoing disadvantages inherent in the known types of lower spine protectors now present in the prior art, the present invention provides a new lower spine protector construction wherein the same can be utilized for protecting the lower spine from injury from blows to the lower back region of a user.

The general purpose of the present invention, which will be described subsequently in greater detail, is to provide a new lower spine protector apparatus and method which has many of the advantages of the lower spine protectors mentioned heretofore and many novel features that result in a new lower spine protector which is not anticipated, rendered obvious, suggested, or even implied by any of the prior art lower spine protectors, either alone or in any combination thereof.

To attain this, the present invention generally comprises a pad with a pocket on a back face of the pad. An insert is inserted into the pocket. Elongate flexible waist strap are outwardly extended from the sides of the pad.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new lower spine protector apparatus and method which has many of the advantages of the lower spine protectors mentioned heretofore and many novel features that result in a new lower spine protector which is not anticipated, rendered obvious, suggested, or even implied by any of the prior art lower spine protectors, either alone or in any combination thereof.

It is another object of the present invention to provide a new lower spine protector which may be easily and efficiently manufactured and marketed.

It is a further object of the present invention to provide a new lower spine protector which is of a durable and reliable construction.

An even further object of the present invention is to provide a new lower spine protector which is susceptible of a low cost of manufacture with regard to both materials and labor, and which accordingly is then susceptible of low prices of sale to the consuming public, thereby making such lower spine protector economically available to the buying public.

Still yet another object of the present invention is to provide a new lower spine protector which provides in the apparatuses and methods of the prior art some of the advantages thereof, while simultaneously overcoming some of the disadvantages normally associated therewith.

Still another object of the present invention is to provide a new lower spine protector for protecting the lower spine from injury from blows to the lower back region of a user.

Yet another object of the present invention is to provide a new lower spine protector which includes a pad with a pocket on a back face of the pad. An insert is inserted into the pocket. Elongate flexible waist strap are outwardly extended from the sides of the pad.

Still yet another object of the present invention is to provide a new lower spine protector that is designed to protect contact sports athletes such as hockey and lacrosse athletes from injury from blows to their lower back by deflecting, dispersing and absorbing the blow. For example, in hockey, the lower spine protector protects the region of the user's back that is exposed between the upper back portion of the user's shoulder pad and the waist portion of the user's padded hockey pants.

Even still another object of the present invention is to provide a new lower spine protector that light weight and does not restrict a user's movement.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic exploded perspective view of the present invention.

FIG. 4 is a schematic cross sectional view of the present invention taken from line 4—4 of FIG. 1.

DESCRIPTION OF THE PREFERRED EMBODIMENT

Figure 1:
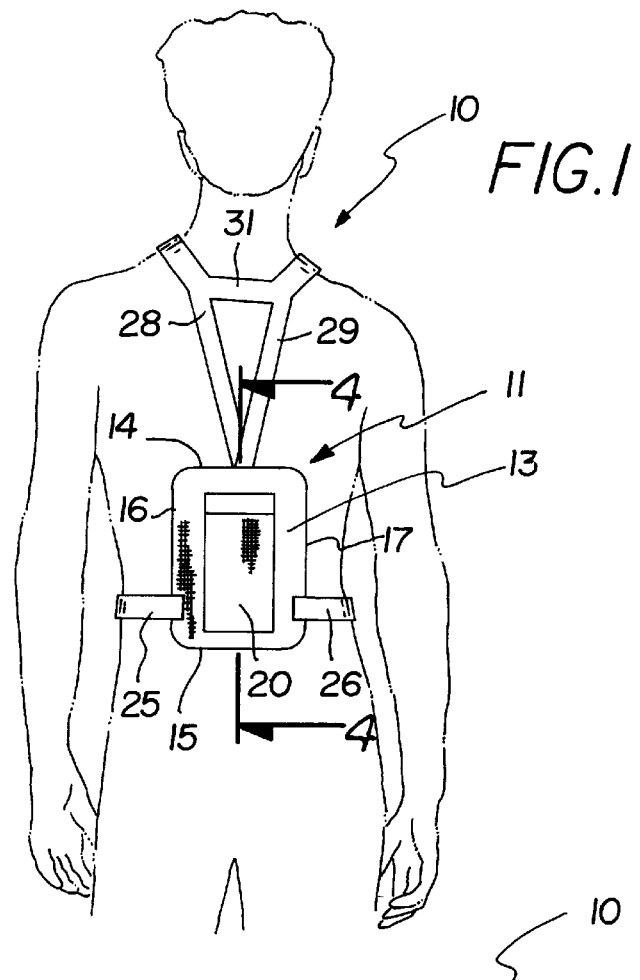
FIG. 1 is a schematic back view of a new lower spine protector in use on a user according to the present invention.

With reference now to the drawings, and in particular to FIGS. 1 through 4 thereof, a new lower spine protector embodying the principles and concepts of the present invention and generally designated by the reference numeral 10 will be described.

As best illustrated in FIGS. 1 through 4, the lower spine protector 10 generally comprises a pad with a pocket on a back face of the pad. An insert is inserted into the pocket. Elongate flexible waist strap are outwardly extended from the sides of the pad.

In use, the lower spine protector is designed for protecting the lower spine region of the back of a user. In closer detail, the lower spine protector 10 comprises a generally rectangular pad 11 has generally rectangular front and back faces 12,13, spaced apart generally straight top and bottom edges 14,15, and a spaced apart pair of generally straight side edges 16,17 extending between the top and bottom edges of the pad. Preferably, the front and back faces of the pad lie in generally parallel planes to one another. In this preferred embodiment, the top and bottom edges of the pad are extended generally parallel to one another and the side edges of the pad are extended generally parallel to one another and generally perpendicular to the top and bottom edges of the pad.

The pad has a thickness defined between the front and back faces of the pad, a height defined between the top and bottom edges of the pad, and a width defined between the side edges of the pad. Preferably, the height of the pad is greater than about twice the width of the pad. Also preferably, the width of the pad is at least four times greater than the thickness of the pad. In an ideal embodiment, the thickness of the pad is about 1½ inches, the height of the pad is about 12 inches, and the width of the pad is about 9 inches.

With reference to FIG. 4, the pad comprises a flexible outer layer 18 substantially covering a resiliently deformable inner core 19 having a thickness several times greater than the outer layer of the pad. Ideally, the outer layer of the pad comprises a flexible nylon fabric material and the inner core of the pad comprises a resiliently deformable open cell foamed material.

In use as best illustrated in FIG. 1, the front face of the pad is designed for positioning against a lower spine region of a back of a user such that the top edge of the pad is upwardly positioned and the bottom edge is downwardly positioned.

The back face of the pad has a generally rectangular pocket 20 with an open top. The pocket comprises a generally rectangular panel coupled to the back face of the pad along an outer perimeter of the panel. The panel preferably comprises a flexible outer layer 21 substantially covering a resiliently deformable inner core 22. Ideally, the outer layer of the panel comprises a flexible nylon fabric material and the inner core of the panel comprises a resiliently deformable closed cell foamed material. Ideally, the panel has a thickness of about ¼ inch.

A resiliently rigid insert 23 is inserted into the pocket. The insert preferably has a generally rectangular outer periphery and is also curved with a concavity facing towards the back face of the pad and a convexity facing outwards from the back face of the pad. As best illustrated in FIG. 3, the concavity and convexity of the insert each have has a radius of curvature lie in a generally horizontal plane when the lower spine protector is worn on the lower spine region of the back of the user. In use, the insert protects the lower spine from blows by deflecting and dispensing the force of the blow while the pad helps to absorb the force of the blow.

Preferably, the pocket has closure closing the open top of the pocket. Preferably, the panel has inner and outer faces with the closure comprising a hook and loop fastener 24 detachably attaching the inner face of the panel adjacent the top of the pocket to the back face of the pad.

Figure 2:
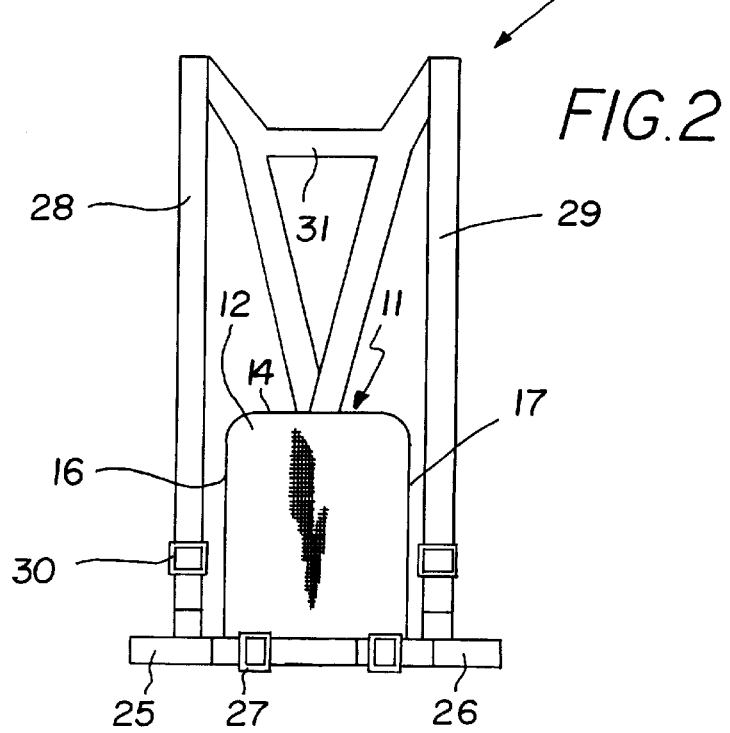
FIG. 2 is a schematic front view of the present invention.

Each of the side edges of the pad has an elongate adjustable-length flexible waist strap 25,26 outwardly extending therefrom. As best illustrated in FIG. 3, each of the waist straps preferably has a first end coupled to the back face of the pad adjacent the associated side edge of the pad. With reference to FIG. 2, the waist straps each have a second end opposite the first end of the respective waist strap which are coupled together preferably by a hook and loop fastener to permit detachment of the second ends of the waist straps from one another. As illustrated in FIG. 1, in use, the waist straps are designed for wrapping around the waist of the user and coupling the second ends of the waist straps in the front of the user. Ideally, the waist straps each have a buckle for adjusting the effective length of the respective waist strap to best fit the waist straps around the waist of a user.

A pair of elongate adjustable-length shoulder straps 28,29 outwardly extend from the top edge of the pad. As best illustrated in FIG. 3, the shoulder straps each have a first end coupled to the top edge of the pad at a generally common central location on the top edge of the pad such that the converge in a direction toward the top edge of the pad. As illustrated in FIG. 2, each of shoulder straps has a second end opposite the first end of the respective strap coupled to an associated waist strap adjacent the second end of the associated waist strap. In use, the shoulder straps are designed for looping over the shoulders of a user as illustrated in FIG. 1 so that the lower spine protector hangs on the user's shoulders. Like the waist straps, ideally, the shoulder straps each have a buckle 30 for adjusting the effective length of the respective shoulder strap to best fit over the shoulders of the user.

Preferably, an elongate flexible upper back strap 31 extends between the shoulder straps. The upper back strap is spaced apart from the first ends of the shoulder straps, the upper back strap is designed for positioning on the upper back region of the user below the neck of the user as illustrated in FIG. 1 to help hold the pad in place on the lower back region of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A lower spine protector, comprising:

a pad having front and back faces, top and bottom edges, and a pair of side edges;

said back face of said pad having a pocket;

an insert being inserted into said pocket;

each of said side edges of said pad having an elongate flexible waist strap outwardly extending therefrom;

a pair of elongate shoulder straps outwardly extending from said top edge of said pad; and wherein said shoulder straps each have a first end coupled to said top edge of said pad at a generally common central location on said top edge of said pad, and wherein each of shoulder straps has a second end opposite said first end of the respective strap, said second end of one of said shoulder straps being coupled to one of said waist straps towards said second end of the associated waist strap, said second end of the other of said shoulder straps being coupled to the other of said waist straps towards said second end of the associated waist strap.

2. The lower spine protector of claim 1, wherein said pad comprises a flexible outer layer substantially covering a resiliently deformable inner core.

3. The lower spine protector of claim 2, wherein said outer layer of said pad comprises a flexible fabric material and said inner core of said pad comprises a resiliently deformable foamed material.

4. The lower spine protector of claim 1, wherein said pocket has an open top and a closure closing said open top of said pocket.

5. The lower spine protector of claim 4, wherein said closure comprises a hook and loop fastener.

6. The lower spine protector of claim 1, wherein said insert is curved and has a concavity facing towards said back face of said pad.

7. The lower spine protector of claim 6, wherein said concavity of said insert has a radius of curvature lying in a generally horizontal plane.

8. The lower spine protector of claim 1, further comprising an elongate flexible upper back strap extending between said shoulder straps, said upper back strap being spaced apart from said first ends of said shoulder straps.

9. A lower spine protector, comprising:

a generally rectangular pad having generally rectangular front and back faces, spaced apart generally straight top and bottom edges, and a spaced apart pair of generally straight side edges extending between said top and bottom edges of said pad;

said front and back faces of said pad lying in generally parallel planes to one another;

said top and bottom edges of said pad being extended generally parallel to one another;

said side edges of said pad being extended generally parallel to one another and generally perpendicular to said top and bottom edges of said pad;

said pad having a thickness defined between said front and back faces of said pad, a height defined between said top and bottom edges of said pad, and a width defined between said side edges of said pad;

wherein said height of said pad is greater than about twice said width of said pad;

wherein said width of said pad is at least four times greater than said thickness of said pad;

said pad comprising a flexible outer layer substantially covering a resiliently deformable inner core, wherein said outer layer of said pad comprises a flexible fabric material and said inner core of said pad comprises a resiliently deformable foamed material;

said front face of said pad being adapted for positioning against a lower spine region of a back of a user;

said back face of said pad having a generally rectangular pocket, said pocket having an open top;

said pocket comprising a generally rectangular panel coupled to said back face of said pad along an outer perimeter of said panel;

said panel comprising a flexible outer layer substantially covering a resiliently deformable inner core, wherein said outer layer of said panel comprises a flexible fabric material and said inner core of said panel comprises a resiliently deformable foamed material;

a insert being inserted into said pocket, said insert having a generally rectangular outer periphery, wherein said insert is curved and has a concavity facing towards said back face of said pad, said concavity of said insert having a radius of curvature lying in a generally horizontal plane;

said pocket having closure closing said open top of said pocket;

said panel having inner and outer faces, wherein said closure comprises a hook and loop fastener detachably attaching said inner face of said panel adjacent said top of said pocket to said back face of said pad;

each of said side edges of said pad having an elongate flexible waist strap outwardly extending therefrom, each of said waist straps having a first end coupled to said back face of said pad adjacent the associated side edge of said pad;

said waist straps each having a second end opposite said first end of the respective waist strap, said second ends of said waist straps being coupled together, wherein a hook and loop fastener detachably couples said second ends of said waist straps together;

a pair of elongate shoulder straps outwardly extending from said top edge of said pad, said shoulder straps each having a first end coupled to said top edge of said pad at a generally common central location on said top edge of said pad;

each of shoulder straps having a second end opposite said first end of the respective strap, said second end of one of said shoulder straps being coupled to one of said waist straps towards said second end of the associated waist strap, said second end of the other of said shoulder straps being coupled to the other of said waist straps towards said second end of the associated waist strap; and an elongate flexible upper back strap extending between said shoulder straps, said upper back strap being spaced apart from said first ends of said shoulder straps.

10. A lower spine protector, comprising:

a pad having front and back faces, top and bottom edges, and a pair of side edges;

said back face of said pad having a pocket;

an insert being inserted into said pocket;

each of said side edges of said pad having an elongate flexible waist strap outwardly extending therefrom;

a pair of elongate shoulder straps outwardly extending from said top edge of said pad; and wherein said shoulder straps each have a first end coupled to said top edge of said pad, and wherein each of shoulder straps has a second end opposite said first end of the respective strap, said second end of one of said shoulder straps being coupled to one of said waist straps towards said second end of the associated waist strap, said second end of the other of said shoulder straps being coupled to the other of said waist straps towards said second end of the associated waist strap.

11. The lower spine protector of claim 10, wherein said pad comprises a flexible outer layer substantially covering a resiliently deformable inner core.

12. The lower spine protector of claim 11, wherein said outer layer of said pad comprises a flexible fabric material and said inner core of said pad comprises a resiliently deformable foamed material.

13. The lower spine protector of claim 10, wherein said pocket has an open top and a closure closing said open top of said pocket.

14. The lower spine protector of claim 13, wherein said closure comprises a hook and loop fastener.

15. The lower spine protector of claim 10, wherein said insert is curved and has a concavity facing towards said back face of said pad.

16. The lower spine protector of claim 15, wherein said concavity of said insert has a radius of curvature lying in a generally horizontal plane.

17. The lower spine protector of claim 10, further comprising an elongate flexible upper back strap extending between said shoulder straps, said upper back strap being spaced apart from said first ends of said shoulder straps.

* * * * *